United States Patent [19]

Leone-Bay et al.

[11] Patent Number: 4,739,057
[45] Date of Patent: Apr. 19, 1988

[54] PROCESS FOR CONVERTING ORGANO-HYDROXYL COMPOUNDS TO HALIDES

[75] Inventors: Andrea Leone-Bay; Elliott Bay, both of Ridgefield, Conn.; Peter E. Timony, Valley Cottage, N.Y.

[73] Assignee: Stauffer Chemical Co., Westport, Conn.

[21] Appl. No.: 880,469

[22] Filed: Jun. 30, 1986

[51] Int. Cl.$^4$ .................. C07D 239/24; C07D 213/24; C07C 19/08; C07C 17/16

[52] U.S. Cl. .................................. 544/334; 546/290; 546/345; 546/303; 546/295; 549/81; 549/504; 568/32; 568/579; 568/656; 570/124; 570/127; 570/182; 570/183; 570/206; 570/207; 570/261

[58] Field of Search ............... 546/345, 290, 303, 295; 544/334; 549/81, 504; 568/32, 656, 579; 570/127, 124, 182, 183, 206, 207, 261

[56] References Cited

PUBLICATIONS

Payne, D. S., The Chemistry of Phosphorus Halides.

*Primary Examiner*—Henry R. Jiles
*Assistant Examiner*—J. Richter
*Attorney, Agent, or Firm*—Joel G. Ackerman

[57] ABSTRACT

A process for converting organic hydroxyl-containing compounds to halides which comprises reacting the hydroxyl-containing compound with a phosphorushalide reagent of formula: $R_nPX_{5-n}$ wherein n is selected from 1, 2 and 3; R is selected from the group consisting of C-6 to C-10 aryl and substituted aryl wherein the substituents are selected from the group consisting of straight and branched chain alkyl, alkoxy, and haloalkyl, halogen, sulfonate and mixtures thereof; and X is a halogen. It is preferred to carry out the reaction in the presence of an arylphosphorusoxydihalide solvent. The use of an arylphosphorustetrahalide and particularly phenylphosphorustetrachloride is preferred. The arylphoshorustetrahalide can be prepared in situ by contacting a solution of the corresponding arylphosphorusdihalide in an arylphosphorusoxydihalide solvent with a halogen. The process can further comprise the step of heating the reaction mixture. Maintaining a reaction temperature of from about 0° C. to about 150° C. for from about 1 hour to about 24 hours is preferred.

10 Claims, No Drawings

PROCESS FOR CONVERTING ORGANO-HYDROXYL COMPOUNDS TO HALIDES

BACKGROUND OF THE INVENTION

1. Field of the Invention

This invention relates to a process for preparing organic halides and in particular to a process for selectively substituting an hydroxyl group with a halogen.

2. Related Information

Alcohols are a very common starting point in organic synthesis, and a common reaction in such an organic synthesis is the conversion of the alcohol into an organic halide. This conversion has usually been effected by the use of hydrogen halides and/or certain phosphorus trihalides.

Various other methods are known for preparing the versatile organic halide intermediate, e.g., the Sandmeyer reaction wherein an aromatic nitro group is reduced to an amine, diazotized, then reacted with copper chloride to yield the corresponding chloroaromatic compound.

The use of aryl phosphorushalides of formula: $R_nPX_{5-n}$ wherein n is selected from 1, 2 and 3; R is selected from the group consisting of C-6 to C-10 aryl and substituted aryl wherein the substituents are selected from the group consisting of: straight and branched chain alkyl, alkoxy, and haloalkyl; halogen, sulfonate and mixtures thereof; and X is a halogen, and particularly the use of phenylphosphorustetrachloride (PPTC), as a reagent for organic synthesis is practically unknown. Timokhin, B. V.; Dmitriev, V. K., Dmitriev, V. I., Zh. Obshch. Khim 1984, 54, 1290, reported the reaction of cyclohexene with PPTC to give trans-1,2-dichlorocyclohexane and 3-chlorocyclohexene. Mitrasov, Y. N.; Vladyko, E. D.; Kormachev, V. V. USSR SU Nos. 1,051,097 and 1,051,096 found that treatment of aliphatic aldehydes and ketones with PPTC produced geminal dichlorides. PPTC has also been used to produce tetrazines from hydrazines, see Yagupol'skii, L. M.; Matyushecheva, G. I.; Mikhailov, V. S.; Bulygina, L. A. USSR SU No. 498,300 and Matyushecheva, G. I.; Mikhailov, V. S. Yagupol'skii, L. M., Zh. Org. Khim, 1974, 10, 124.

SUMMARY OF THE INVENTION

An object of this invention is to provide a process for simply preparing organic halides by selectively substituting an hydroxyl group with a halogen group.

A further object of this invention is the use of an arylphosphorushalide, and particularly an arylphosphorushalide such as PPTC, as a reagent in organic synthesis and particularly its use as a selective halogenating agent in the preparation of organic halides.

Other objects and advantages of the present invention are described elsewhere within this specification.

This invention is a process for converting an organic hydroxyl-containing compound to the corresponding organic halide which comprises reacting the hydroxyl-containing compound with an arylphosphorushalide of formula: $R_nPX_{5-n}$ wherein n is selected from 1, 2 and 3; R is selected from the group consisting of C-6 to C-10 aryl and substituted aryl wherein the substituents are selected from the group consisting of: straight and branched chain alkyl, alkoxy, and haloalkyl; halogen, sulfonate and mixtures thereof; and X is a halogen, in an amount effective to convert the hydroxyl-containing compound to the halide. In this process, a preferred arylphosphorushalide, e.g., an arylphosphorustetrahalide, can be prepared in situ by contacting a solution of an arylphosphorusdihalide in an arylphosphorusoxydihalide solvent with a halogen. In preferred embodiments, the hydroxyl-containing compound is added to a solution containing the arylphosphorushalide and the resulting reaction mixture is heated. Maintaining a reaction temperature of from about 0° C. to about 150° C. for from about 1 hour to about 24 hours is preferred. Phenylphosphorustetrahalide is a preferred arylphosphorustetrahalide and particularly the chloride which is used to prepare the corresponding organic chloride product.

DETAILED DESCRIPTION OF THE INVENTION

In the process of this invention, organic hydroxyl groups are removed and replaced with halogens. The major product resulting, has the hydroxyl group replaced by a halogen, i.e., after the hydroxyl group is removed, thus this process is one for selectively substituting an hydroxyl group with a halogen.

The hydroxyl-containing compound useful in this invention is an organic hydroxyl-containing compound. This compound can be a hydrocarbyl or an heterocyclic. The hydrocarbyl can be aliphatic or aromatic and the aliphatic can be straight or branched chain, cyclic or bridged. The heterocyclic can be four to ten-membered heterocyclic rings having 1 to 2 hetero-atom(s) selected from nitrogen, oxygen and sulfur.

Preferred hydroxyl-containing compounds are of the formula $R^1OH$ wherein $R^1$ is selected from the group consisting of straight and branched chain, cyclic and bridged alkyl having 1 to 25 carbon atoms. Particularly preferred compounds are tertiary alcohols.

Illustrative hydroxyl-containing compounds include, but are not limited to, aliphatic and aromatic alcohols, hydroxyl-substituted; aryls; pyrimidines; pyridines; anthracenes; furans; thiophenes and pyrans.

The aryl phosphorushalide useful in this invention preferably has the formula:

$R_nPX_{5-n}$ wherein n, R and X are defined above. A preferred compound is an arylphosphorus halide such as an arylphosphorustetrahalide and particularly an arylphosphorustetrahalide prepared in situ by contacting a solution of an arylphosphorusdihalide in an arylphosphorusoxydihalide solvent with a halogen.

The aryl portion of arylphosphorustetrahalide, arylphosphorustrihalide, arylphosphorusdihalide, and arylphosphorusoxydihalide can be C-6 to C-10 aryl and substituted aryl wherein the substituents can be selected from the group consisting of: straight and branched chain alkyl, alkoxy, and haloalkyl; halogen, sulfonate and mixtures thereof. The halide portions of these compounds can be any of the halogens, e.g., chlorine, bromine, iodine, and fluorine, with chlorine being preferred.

In this process, the hydroxyl-containing compound is contacted with, for example, the preferred arylphosphorustetrahalide in the presence of an arylphosphorusoxydihalide solvent and in an amount effective to remove the hydroxyl group from the hydroxyl-containing compound and replace it with a halogen group. The aryl phosphorushalide can be prepared by any known method, and the preferred arylphosphorustetrahalide can preferably be prepared in situ by contacting a solution of an arylphosphorusdihalide in the solvent, arylphosphorusoxydihalide, with a halogen. In this preferred procedure, it is preferred to use a particular aryl halide and the corresponding halogen throughout the preparation, e.g., in the preparation of phenylphosphorustetrachloride, phenylphosphorusdichloride in a solution of phenylphosphorusoxydichloride is contacted with chlorine gas. It is also preferred that the hydroxyl-containing compound be added to the solution containing the arylphosphorushalide.

It is believed that the mere contacting of the hydroxyl-containing compound and the arylphosphorushalide in the presence of an arylphosphorusoxydihalide solvent can result in the preparation of certain quantities of the desired halide end-product. However, heating the reaction mixture over a period of time can result in increased yields. Maintaining the reaction mixture at a temperature from about 0° C. to about 150° C. for from about 1 hour to about 24 hours is preferred and a temperature range of from about 50° C. to about 120° C. maintained for about 5 hours is particularly preferred. The reactants utilized in the process of the present invention are generally employed in stoichiometric amounts, although an excess of any reagent can be used, if desired. The quantity of undesired side products, however, can be minimized by the use of approximately stoichiometric amounts of reactants. No catalyst is used or is necessary in the processes of the present invention.

The process of this invention can proceed in the absence of a solvent, however, the product yield would be expected to be low. Therefore, the use of a solvent is expected to promote better yields. A solvent in which either reagent or both reagents are soluble can be used, e.g., chlorobenzene, ethylene dichloride, dimethylsulfoxide, etc. Preferred solvents are arylphosphorusoxydihalides.

The reaction times can vary over relatively wide ranges and can easily be determined by one of ordinary skill in the art. Factors affecting reaction time can include the choice of a specific reactant and a specific reaction temperature. Increases in temperature and increases in reactant concentrations up to stoichiometric amounts can result in decreased reaction times. Dilute reactants usually require longer reaction time than the more concentrated reactions. The reaction is run at atmospheric pressure and it is believed that increased pressure can increase the reaction rate.

The following generalized equation represents the process of this invention:

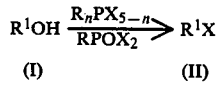

$R_nPX_{5-n}$ is the arylphosphorushalide and $RPOX_2$ is the arylphosphorusoxydihalide solvent which are both described above. Formula (I) represents the hydroxyl-containing compound, here depicted containing only one hydroxyl group for clarity. Formula (II) represents the resulting halogenated product in which the hydroxyl group is replaced by the halogen X.

The following experiments describe various embodiments of this invention. Other embodiments will be apparent to one of ordinary skill in the art from a consideration of this specification or practice of the invention disclosed herein. It is intended that the specification and experiments be considered as exemplary only, with the true scope and spirit of the invention being indicated by the claims which follow the experiments.

EXPERIMENTS

The following experiments demonstrate the use of phenylphosphorustetrachloride (PPTC) in benzenephosphorusoxydichloride (BPOD) to convert hydroxyl-containing compounds to chlorides.

General Procedure for the Preparation of Chlorides from Alcohols by use of Phenylphosphorus Tetrachloride Chloride gas (10 mM) was bubbled into a solution of phenyldichlorophosphine (10 mM) in BPOD (18 mL). External cooling was sometimes necessary to keep the reaction temperature below 30° C. throughout the chlorine addition. The alcohol (10 mM) was then added at or below room temperature (TABLE I) and the reaction maintained at the conditions specified in TABLE I. When the reaction was completed, the reaction mixture was poured onto ice/water (50 mL) and neutralized with 50% aqueous sodium hydroxide. This aqueous mixture was then extracted with three 30 mL portions of ether. The combined ether extracts were washed with brine, dried over anhydrous magnesium sulfate and concentrated in vacuo to give the desired product in good yield.

TABLE I below summarizes the results obtained using PPTC in BPOD to prepare chlorides from various alcohols following the procedure described above.

TABLE 1

| Exp. No. | Starting Material | Conditions |
|---|---|---|
| 1. | n-hexanol | 25° C.; 6 hrs. |
| 2. | benzyl alcohol | 0° C.; on mixing |
| 3. | 6-chloro-2-pyridinol | 100° C.; 6 hrs. |
| 4. | i-pentanol | 25° C.; 12 hrs. |
| 5. | neopentanol | 25° C.; 12 hrs. |
| 6. | s-pentanol | 50° C.; 12 hrs. |
| 7. | (R)—(—)-2-octanol | 25° C.; on mixing |
| 8. | t-butanol | 50° C.; 12 hrs. |
| 9. | norborneol | 25° C.; 12 hrs. |
| 10. | 2-pyrimidinol | 120° C.; 4 hrs. |
| 11. | phenol | 100° C.; 12 hrs. |
| 12. | cyclopropylmethanol | 0° C.; on mixing |

| Exp. No. | Product | Yield Wt. % |
|---|---|---|
| 1. | n-hexylchloride | 77 |
| 2. | benzyl chloride | 72 |
| 3. | 2,6-dichloropyridine | 80 |
| 4. | i-pentylchloride | 44 |
| 5. | neopentylchloride | 55 |
| 6. | s-pentylchloride | 80 |
| 7. | (S)—(—)-2-octylchloride | 85 (94% inversion) |
| 8. | t-butylchloride | 97 |
| 9. | norbornyl chloride | 60 |
| 10. | 2-chloropyrimidine | 62 |
| 11. | chlorobenzene | 93 |
| 12. | cyclopropylmethylchloride | 98 |

What is claimed is:

1. A process for converting an organic hydroxyl-containing compound to the corresponding halide which comprises reacting the hydroxyl-containing compound with an arylphosphorushalide reagent of formula: $R_nPX_{5-n}$ wherein n is selected from 1, 2 and 3; R is selected from the group consisting of C-6 to C-10 aryl and substituted aryl wherein the substituents are selected from the group consisting of straight and branched chain alkyl, alkoxy, ahd haloalkyl, halogen, sulfonate and mixtures thereof; and X is a halogen, in an amount effective to convert the hydroxyl-containing compound to the halide.

2. The process of claim 1 wherein the hydroxyl-containing compound is of formula $R^1OH$ wherein $R^1$ is selected from the group consisting of straight and branched chain cyclic and bridged alkyl having 1 to 25 carbon atoms, aryl, pyrimidine, pyridine, anthracene, furan, thiophene and pyran.

3. The process of claim 1 wherein the arylphosphorus halide is an arylphosphorustetrahalide prepared in situ by contacting a solution of an arylphosphorusdihalide in an arylphosphorusoxydihalide solvent with a halogen gas.

4. The process of claim 3 wherein the hydroxyl-containing compound is added to the solution containing the arylphosphorustetrahalide.

5. The process of claim 4 which further comprises the step of heating the mixture resulting from the addition of the hydroxyl-containing compound.

6. The process of claim 4 wherein the resulting mixture is maintained at a temperature of from about 0° C. to about 150° C. for from about 1 hour to about 24 hours.

7. The process of claim 6 wherein the arylphosphorustetrahalide is phenylphosphorustetrahalide.

8. The process of claim 7 wherein the phenylphosphorustetrahalide is prepared in situ by contacting a solution of phenylphosphorusdihalide in a phenylphosphorusoxydihalide solvent with a halogen.

9. The process of claim 8 wherein the halides are selected from the group consisting of chlorides, bromides, iodides, fluorides and mixtures thereof and the halogen is selected from the group consisting of chlorine, bromine, iodine, fluorine and mixtures thereof.

10. The process of claim 8 wherein the halides are chlorides and the halogen is chlorine.

* * * * *